United States Patent [19]

Hoseney et al.

[11] Patent Number: 5,280,717
[45] Date of Patent: Jan. 25, 1994

[54] ADHESION TESTING APPARATUS AND METHOD FOR FLOWABLE MATERIALS SUCH AS WHEAT DOUGHS

[75] Inventors: Russell C. Hoseney; Wei Z. Chen, both of Manhattan, Kans.

[73] Assignee: Kansas State University Research Foundation, Manhattan, Kans.

[21] Appl. No.: 961,121

[22] Filed: Oct. 14, 1992

[51] Int. Cl.$^5$ .............................................. G01N 11/00
[52] U.S. Cl. ........................................ 73/54.22; 73/169
[58] Field of Search ................... 73/54.22, 169, 64.48; 426/231

[56] References Cited

U.S. PATENT DOCUMENTS

| | | | |
|---|---|---|---|
| 1,441,564 | 1/1923 | Eberly | 73/54.22 |
| 2,156,407 | 5/1939 | Stewart | 73/54.22 |
| 2,801,537 | 8/1957 | Kabelitz | 73/54.22 |
| 3,169,395 | 2/1965 | Enoch et al. | 73/169 |
| 3,732,724 | 5/1973 | Heinz | 73/169 |
| 4,565,089 | 1/1986 | Arciszewski et al. | 73/169 |
| 4,838,081 | 6/1989 | Finley et al. | 73/169 |

FOREIGN PATENT DOCUMENTS

| | | | |
|---|---|---|---|
| 1050086 | 2/1959 | Fed. Rep. of Germany | 73/58 |
| 0646223 | 2/1979 | U.S.S.R. | 73/169 |
| 0934370 | 6/1982 | U.S.S.R. | 73/169 |

OTHER PUBLICATIONS

A. T. S. Babb et al., "An In-line Consistency Meter for Dough-like Materials", *Measurement and Control*, vol. 3, Nov. 1970, pp. T173–T180.

Dexter, et al.—Grain Research Laboratory Compression Tester: Instrumental Measurement of Cooked Spaghetti Stickiness[12]; Cereal Chemistry, vol. 60 No. 2 1983.

Voisey, et al.—Measuring the Texture of Cooked Spaghetti, Exploratory work on Instrumental Assessment of Stickiness and its Relationship to Microstructure; J. Inst. Can. Sci. Technol Aliment, vol. 11, No. 4, Oct. 1978.

*Primary Examiner*—Robert J. Warden
*Assistant Examiner*—Laura E. Collins
*Attorney, Agent, or Firm*—Hovey, Williams, Timmons & Collins

[57] ABSTRACT

An improved adhesion testing apparatus (20) for the accurate, quantitative measurement of adhesion of coherent flowable materials such as doughs is provided which includes an extrusion-type sample holding device (42) together with a shiftable probe (38). The device (42) includes a base (46) threadably interconnected with a top (48), the latter supporting an extrusion screen (50). In use, a dough sample placed within the base (46) is extruded through the screen (50) in order to present a test portion (92) above the screen (50); the plunger (38) is then lowered into contact with the portion (92), and rapidly withdrawn. The force required to separate the plunger (38) from the test portion (92) is recorded as a measure of adhesion. Provision of the screen (50) essentially eliminates the potentially interferring factor of dough flow in the measurement of adhesion.

15 Claims, 2 Drawing Sheets

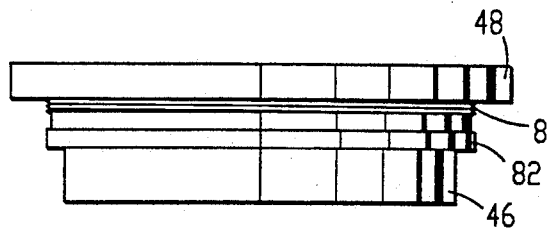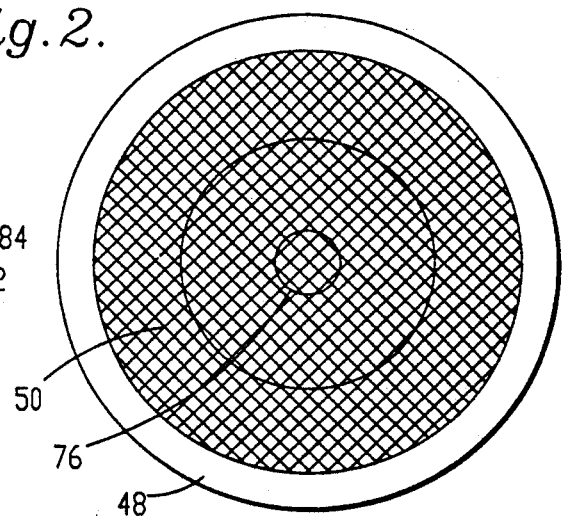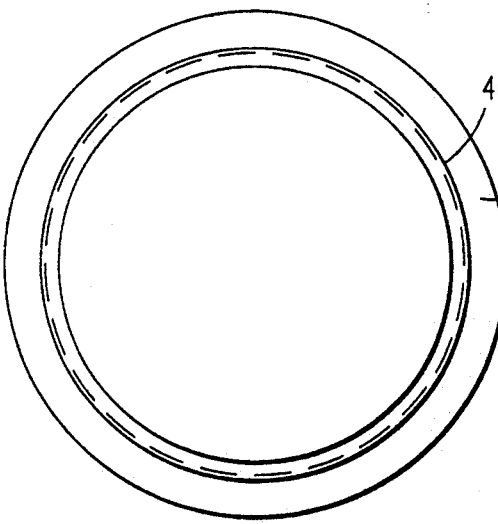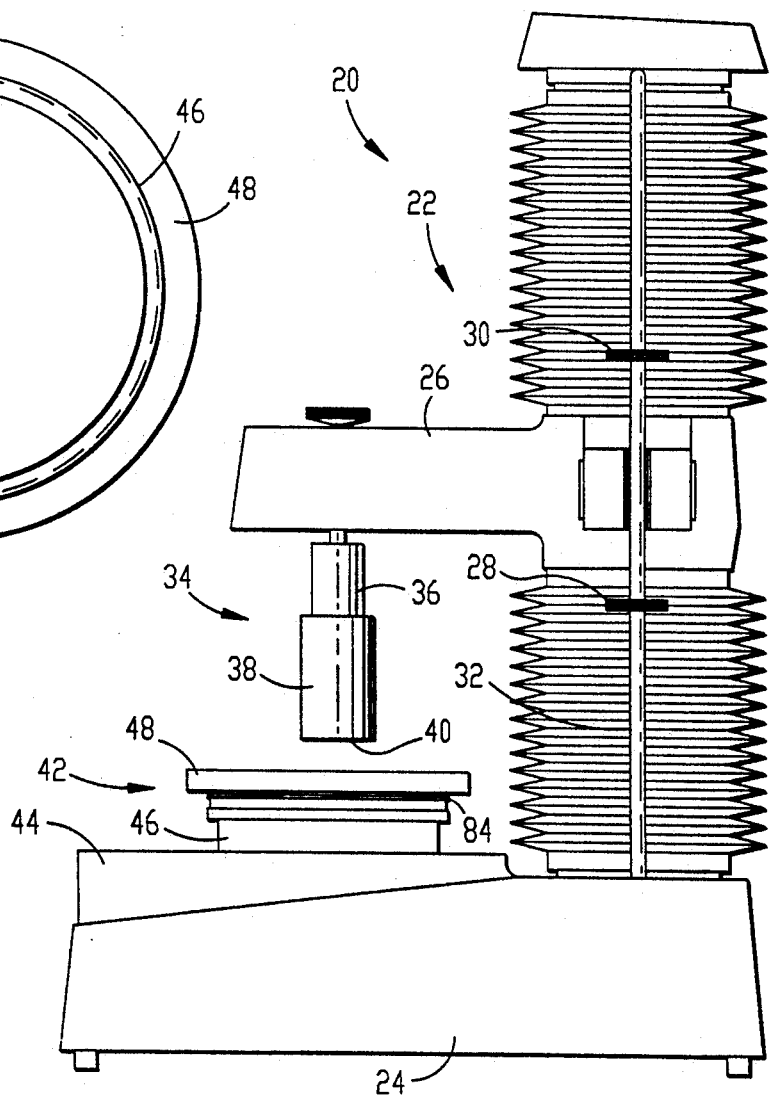

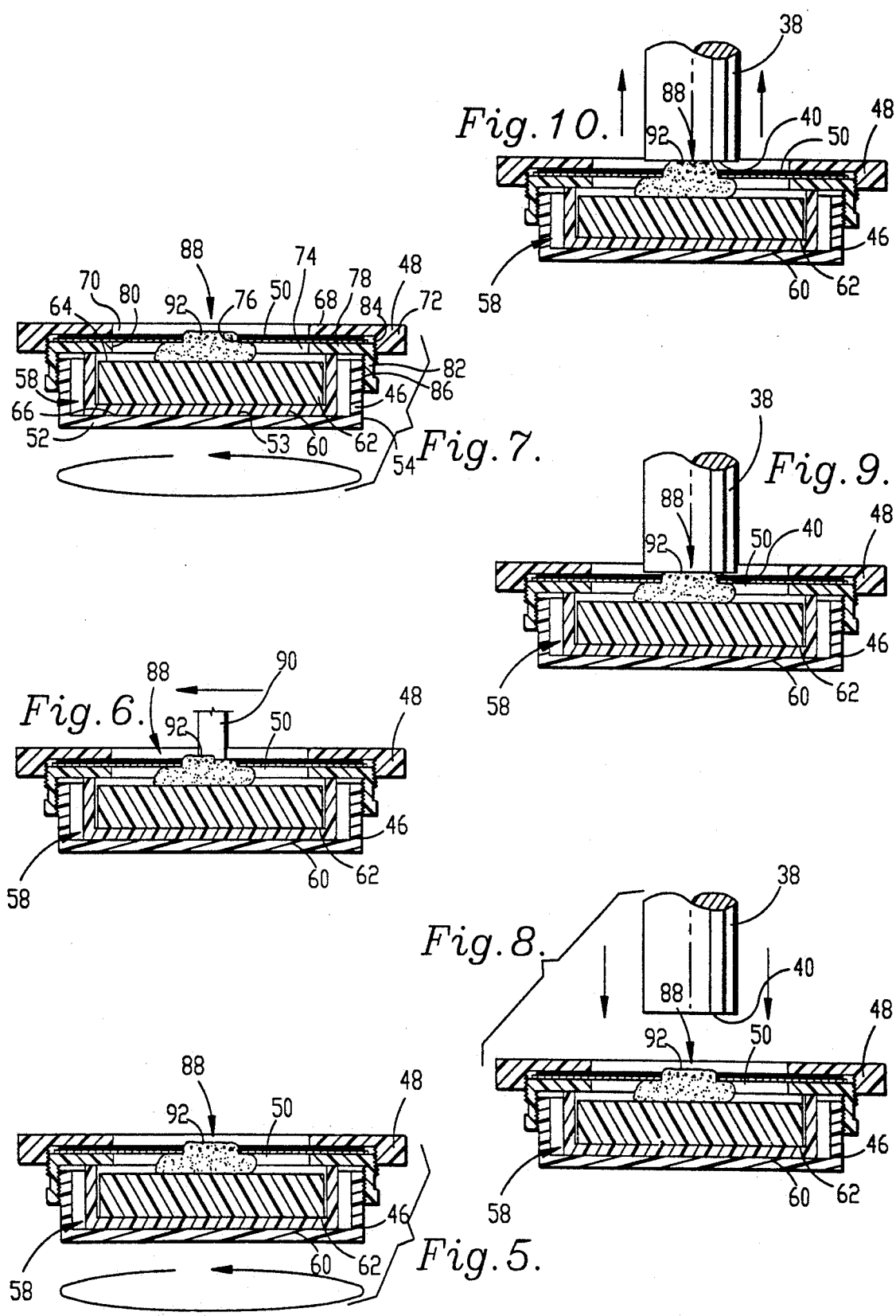

ADHESION TESTING APPARATUS AND METHOD FOR FLOWABLE MATERIALS SUCH AS WHEAT DOUGHS

BACKGROUND OF THE INVENTION

1. Field of the Invention

The present invention is broadly concerned with an improved method and apparatus for the adhesion testing of coherent flowable materials such as doughs. More particularly, it is concerned with such a method and apparatus for the accurate, direct measurement of adhesion or "stickiness" of such materials, while eliminating interfering factors such as the flow and coherence strength thereof.

2. Description of the Prior Art

Instruments for measuring adherence of different types of adhesive materials are commercially available. These devices normally include a probe which is compressed against the surface of the material being tested, followed by withdrawal of the probe at a fixed speed. The force required to separate the probe from the adhesive surface is recorded as a measure of stickiness or adhesion.

However, instruments of this type are not directly applicable for adhesion measurements of flour doughs or other types of coherent materials. When the probe is brought into contact with the surface of a sticky dough, and then pulled away, the dough will often stick to the probe and undergo flow. As the plunger is continuously withdrawn from the sample, the dough stretches and flows, and eventually breaks at a point midway between the probe and the dough mass. As a result, the coherence force that accounts for dough strength holding the dough together is actually measured, rather than stickiness or adherence.

Doughs exhibiting undo stickiness can present a very significant problem to commercial bakers. A very sticky dough can over a relatively short period of time completely clog dough handling equipment, to the point requiring frequent shut-down and clean up of the equipment. These problems are particularly acute with certain recently developed, disease-resistant wheats having a 1B/1R translocation. Some flours derived from such strains give very sticky doughs, even when the flour is given optimum mixing time and water absorption during dough formation.

As a consequence of these developments, commercial bakers are in need of data accurately reflecting the stickiness or adherence characteristics of doughs made from different types of flours, so that informed decisions can be made about the desirability of purchasing specific flours. Despite this need, however, there has heretofore been no accurate means of measuring adherence of coherent flowable materials such as doughs.

SUMMARY OF THE INVENTION

The present invention overcomes the problems outlined above, and provides an adhesion testing apparatus including an improved sample holding device which, in conjunction with a test probe, accurately measures adherence.

Broadly speaking, the overall testing apparatus includes a sample holding device in the form of a base adapted to hold a sample of flowable material to be tested, and a top presenting a perforate screen located above the base and sample, through which a test portion of the material is extruded. A testing probe is located adjacent the screen, and means is provided for effecting relative shifting movement between the device and probe in order to first cause the probe to contact the extruded test portion, and to thereafter shift the probe away from the portion for testing of adhesion. The presence of the perforate screen prevents flow of the material and thereby essentially eliminates the factor of dough strength in the measurement. This in turn gives a test result which accurately measures the desired parameter of adhesion.

In preferred forms, the sample holding device includes means for selective relative movement between the base and perforate screen, in order to effect extrusion of the test portion. To this end, a threaded interconnection is provided between the base and screen so that the base may be selectively shifted toward the screen, thereby extruding a test portion of the material supported by the base through the screen. In order to eliminate undesirable twisting of the dough as the base and top are threaded together, the base includes a sample-supporting insert element which transmits axial extrusion forces to the sample, but slips relative to the base.

The top section of the sample holding device preferably includes a rigid metallic, apertured backing plate adjacent the underside of the screen. The plate aperture defines the section of the screen through which the test portion is extruded; this section is advantageously smaller in area than the adjacent face of the test probe.

In the use of the apparatus of the invention, a sample of coherent flowable material to be tested (e.g., a wheat dough) is placed on the insert element carried by the base. The base is then carefully threaded into the top section of the sample holder in order to extrude a small test portion of the material through the perforate screen. The test probe is then moved into contact with the extruded test portion in order to adhere the proximal face of the probe to the latter. The probe is then quickly shifted away from the screen and the adhesion force is determined.

BRIEF DESCRIPTION OF THE DRAWINGS

FIG. 1 is a side elevational view of a commercially available texture analyzer, shown in conjunction with a probe and sample holding device in accordance with the invention;

FIG. 2 is a plan view of the sample holding device;

FIG. 3 is a side elevational view of the sample holding device;

FIG. 4 is a bottom view of the sample holding device;

FIG. 5 is a vertical sectional view of the sample holding device, illustrating use thereof with a test sample of dough loaded therein;

FIG. 6 is a view similar to that of FIG. 5, but shown in the next step in the preferred usage of the sample holding device;

FIG. 7 is a view similar to that of FIG. 6, and depicting the secondary extrusion of the test sample through the perforate top screen, in order to present a test portion for adhesion testing;

FIG. 8 is a fragmentary, vertical sectional view, illustrating the movement of the test probe towards the extruded test portion;

FIG. 9 is a view similar to that of FIG. 8, and showing the underside of the probe in contact with the test portion; and FIG. 10 is a view similar to that of FIG. 9, which illustrates withdrawal of the test probe in order to determine the adhesion characteristics of the sample.

DETAILED DESCRIPTION OF THE PREFERRED EMBODIMENTS

Turning now to the drawings and particularly FIG. 1, an adhesion or "stickiness" testing device 20 is illustrated. The device 20 includes a commercially available TA.XT2 texture analyzer 22 commercialized by Texture Technologies Corporation of Scarsdale, N.Y. The analyzer 22 includes a base 24 supporting a vertically shiftable, horizontally extending load cell cross arm 26 in an elevated position above the base 24. Movement of the cross arm 26 is limited by, stops 28, 30 located on upright spindle 32. Movement of the cross arm 26 is controlled through a separate console and stepper motor (not shown), and an appropriate recorder (also not shown) is coupled via the console in order to determine forces experienced by the load cell.

An elongated, probe 34 is secured to the outer end of cross arm 26 and depends therefrom; the probe includes a metallic connection block 36, as well as a lower, plexiglass element 38 presenting a lowermost, circular, flat sample contacting face 40.

The overall testing apparatus 20 further includes a sample holding device 42 which rests on the upper test bed surface 44 of base 24 beneath probe 34. Broadly, the sample holding device 42 includes a base 46 as well as a top 48 presenting a perforate screen 50. The screen 50 would normally have an opening size ranging from about 700-4000 microns, with the most preferred screen having an opening size of 1524 microns. As best seen in FIGS. 5-10, the base 46 is in the form of a cup-like, open top member presenting a bottom wall 52 with an upper surface 53, as well as an upstanding peripheral sidewall 54 which is externally threaded adjacent its upper end as at 56. The base 46 is moreover adapted to receive a cylindrical filler element 58 made up of a pair of interfitted cap members 60, 62. The inner cap member 62 presents an uppermost, sample-supporting surf ace 64, whereas the lower surface 66 of the outer cap member 60 is adopted to freely slide on the surface 53 of bottom wall 52.

The top 48 includes an uppermost, annular wall section 68 presenting a central opening 70 therethrough, as well as an outermost, downwardly extending, internally threaded flange 72. The screen 50 is in direct engagement with the underside of wall section 68, and is sized to completely cover the opening 70. A rigid metallic, annular backing plate 74 having a relatively small central opening 76 therethrough is provided beneath screen 50 as shown. The backing plate and screen are retained against upper wall segment 68 by means of an annular connector wall 78 having an opening 80 therethrough corresponding with opening 70. The connector wall includes a depending, circular flange wall 82 which is externally threaded adjacent its upper end as at 84, and internally threaded as at 86 at its lower end. As best seen in FIGS. 5-10, the connector wall 78 is threaded into flange 72 in order to firmly retain backing plate 74 and screen 50 in place, whereas base 46 is threaded into the connector wall through mating engagement of the threads 86. As can be appreciated, as the base 46 is threaded into connector wall 78, the filler element 58 is likewise moved toward screen 50.

Attention is next directed to FIGS. 5-10, which illustrate the preferred use of the device 42 in conjunction with analyzer 22. In the first step (see FIG. 5), the base 46 is loaded with a sample 88 of flowable material, such as a wheat flour dough. At this point, the cap 46 is threaded into connector wall 78 as described, until the upper portion of the dough sample extrudes through the screen 50, in the region thereof defined by central opening 76 of backing plate 74. Thereafter, a spatula 90 or similar device is used to scrap the upper surface of the screen 50 (see FIG. 6), and the base 46 is carefully threaded upwardly so as to extrude a test portion 92 through the screen 50.

At this point, the analyzer 22 is operated so as to lower test probe 38 toward the test portion 92, as shown in FIG. 8. The probe 38 is lowered until the face 40 comes into full and complete contact with the test portion, but before engagement is made with the screen 50. This insures that an adhesive contact is established between the probe and test portion. At this point (see FIG. 10), the probe 38 is elevated as rapidly as possible away from screen 50 until adhesive contact between the face 40 and test portion 92 is broken. When this occurs, the load cell associated with the analyzer 22 experiences a sharp drop in applied force, which is correlated with the force required to separate the plunger surface from the test portion. This enables an accurate quantitative determination of adhesion to be made. Generally, the above procedure is repeated two additional times, and the final adhesion value for a given sample is determined as the average of the three replications.

EXAMPLE

In this test, a total of 18 doughs made from flours derived from different wheat strains were tested, using the apparatus described above. The wheat samples were milled using a Ross experimental mill in the Department of Grain Science and Industry at Kansas State University. The moisture contents, optimum mixing times and water absorptions of each flour sample were measured using AACC Approved Methods 44-15 and 54-40.

The TA.XT2 library program #3 (adhesives test) was used. The compression force selected was 40 grams-force. The test plunger had a lower, 25 mm surface. The trigger force used was set at 5 grams-force. The downward travel speed for the plunger was set at 2 mm/sec., whereas the withdrawal speed of the plunger was set at 10 mm/sec. The holding time where the plunger was maintained at its lowermost, dough-contacting position was 0.1 sec., and the plunger travel distance was set at 4 mm. The extrusion screen had 14 openings per inch with an opening size of 1524 microns.

Ten grams of each flour sample was mixed with an optimum amount of water, and mixed in a mixograph to its optimum. The dough sample was then transferred to the sample holding device 42, and particularly was placed on the surface 64 of cap member 62. The base 46 was then threaded into the connector wall 78 until dough extruded through the central region of the screen 50 defined by backing plate opening 76. A sharp blade was used to cut the extruded dough off of the screen surface. A cover was then placed on the test device to minimize moisture loss from the dough surface, and the dough was further extruded out of the screen until a 1 mm thick test portion was formed. The extrusion of the dough was terminated by threading the base 46 backwardly until the base was about to separate from the connector wall. The prepared dough test sample was then allowed to rest for 30 sec. to release the stress produced by the extrusion.

The moisture cover was then removed, and the device 42 was placed beneath the plunger 38 in the texture analyzer. The latter was operated to move the plunger downwardly into contact with the prepared dough test portion, and then withdrawn, in accordance with the parameters described previously. Withdrawal of the plunger at the maximum rate gave the dough samples less time to flow. The force required for separating the plunger from the dough test portion was recorded. The prepared dough surface was again cut using a blade, and the procedure was repeated two additional times. The extrusion/cutting/re-extrusion and measurement procedure was then repeated two additional times. The three dough stickiness readings obtained were averaged and this mean value was recorded as the dough stickiness or adhesion for the individual dough. In order to measure dough stickiness produced by a given flour, three doughs were made from each flour. The dough stickiness of each dough was measured, and the mean of the dough stickiness values of the three doughs was recorded as the dough stickiness produced by the flour.

The gram-force dough stickiness values obtained in this series of tests are set forth in the following table, which also lists standard deviations.

TABLE

| Wheat | Dough Stickiness (gram-force) |
| --- | --- |
| Hard Red Winter Wheat | 30 ± 1 |
| Frank Filipi, Narha, KS RP-12 | 54 ± 1 |
| Bruce Regac. Brainard (Siouxland) | 54 ± 1 |
| Century | 65 ± 2 |
| Richard Kubik Prague, Siouxland (strong gluten) | 84 ± 2 |
| Ray Poehler Cairo (strong gluten) Siouxland (HRW) | 85 ± 2 |
| Siouxland R.O.6 | 94 ± 2 |
| Stan, Pavelka, Sr. Bladen (Siouxland) | 106 ± 3 |
| Siouxland D.B.30 | 126 ± 4 |
| YC-13 Siouxland Wheat | 130 ± 6 |
| Siouxland 0B48 | 132 ± 4 |
| Siouxland HW Iureed Culan. Hemingford, Blankenships test plot UOACC, KS 1988 | 161 ± 5 |
| Unknown | 167 ± 5 |
| Siouxland Ylenn Montogomerry | 179 ± 7 |
| YC-23 Siouxland Wheat | 183 ± 7 |
| Kriesel, Cert. Reg. Siouxland | 212 ± 10 |
| Unknown | 278 ± 13 |

The 18 doughs were also given a subjective "feel" test for stickiness. The first four doughs listed above were rated as non-sticky, whereas the next 10 doughs were deemed to sticky, and the last four doughs were rated very sticky.

What is claimed is:

1. Adhesion testing apparatus, comprising:
sample holding device including a base adapted to hold a sample of flowable material to be tested, and a top with a perforate screen located above said base and sample whereby a test portion of said sample of flowable material is extruded through said screen; means for holding said screen stationary during adhesion testing whereby said screen substantially prevents flow of the sample during testing;
a testing probe located adjacent said screen and test portion; and
means operably coupled to at least one of said testing probe and sample holding device for effecting relative shifting movement between said sample holding device and probe in order to first cause said probe to contact said test portion, and to thereafter shift the probe away from said test portion for testing adhesion of said material.

2. The testing apparatus of claim 1, wherein said sample holding device further includes means for selective relative movement between said base and screen in order to cause extrusion of said test portion through said screen.

3. The testing apparatus of claim 2, wherein said means for selective relative movement between said base and screen comprises a threaded interconnection between said base and top, said base having a material-supporting element therein.

4. The testing apparatus of claim 1, wherein said means for effecting relative shifting movement between said sample holding device and said probe includes means operably coupled with said probe for first lowering of said probe into contact with said test portion, and for thereafter elevating said probe.

5. The testing apparatus of claim 1, wherein said probe includes a substantially planar underside adjacent said test portion, said underside having an area greater than the portion of said screen through which the test portion is extruded.

6. The testing apparatus of claim 1, wherein said screen includes a surface remote from said probe, said top including a rigid backing plate having an aperture therethrough and contacting said surface of said screen remote from said probe, said aperture defining a section of said screen through which said test portion is extruded.

7. A sample holding device for a flowable material in order to facilitate adhesion testing of the material, said sample holding device comprising:
a base adapted to hold a sample of flowable material;
a top including a perforate screen located above said base and sample; and
means operably coupling said base and top for selective relative shifting movement of at least one of said base and top in order to extrude a test portion of said material through said screen,
said coupling means including means for holding said screen stationary during adhesion testing whereby said screen substantially prevents flow of the sample during such testing.

8. The sample holding device of claim 7, wherein said means for selective relative shifting movement between said base and screen comprises a threaded interconnection between said base and top for permitting selective movement of the base towards said screen.

9. The sample holding device of claim 8, further comprising a material-supporting element carried by said base and being axially shiftable in response to selective movement of the base towards the screen.

10. The sample holding device of claim 7, wherein said screen includes a surface remote from said probe, said top including a rigid backing plate having an aperture therethrough and contacting said surface of said screen remote from said probe, said aperture defining a section of said screen through which said test portion is extruded.

11. A method of adhesion testing a sample of coherent flowable material, comprising the steps of:
providing a perforate screen;
extruding a test portion of material through said screen, and thereby substantially preventing flow of the material during testing;

contacting said test portion with an adhesion probe, and causing the test portion and probe to adhere; and shifting said probe away from said test portion in order to determine adhesion of said sample.

12. The method of claim 11, wherein said material comprises an edible dough.

13. Testing apparatus for measuring adhesion of a sample comprising:

means defining a surface for supporting a sample thereon;

means operably associated with said means defining said surface and positioned proximal to the sample for engaging the sample, restraining the sample against said surface, and substantially preventing flow of the sample during testing, said means for restraining said sample including apertured means;

probe means proximal to said sample and including a sample-engaging surface;

means operably coupled with said probe means for selective sample testing movement of said sample-engaging surface toward and into contact with said sample, and for disengagement of said sample-engaging surface and sample; and means operably coupled with said probe for measuring a parameter correlated with the force required for disengaging said sample-engaging surface from said sample.

14. The testing apparatus of claim 13, whereby said means for restraining said sample comprises a stationary perforate screen located above said support surface.

15. A method of measuring the adhesiveness of a sample, comprising the steps of:

providing a supporting surface;

placing a sample in contact with the supporting surface;

positioning an apertured restraining member in engagement with the sample for holding the sample against the supporting surface and substantially preventing flow of the sample during testing, a portion of the sample adjacent the aperture including a test region;

providing a sample-engaging probe;

shifting said probe into engagement with said test region of said sample, and causing adherence between the probe and test region;

shifting said probe out of engagement with the test region; and measuring a parameter correlated with a force required for disengaging said probe from said test region.

* * * * *